United States Patent [19]

Hughes

[11] Patent Number: 4,581,435

[45] Date of Patent: Apr. 8, 1986

[54] ALKYL-SUBSTITUTED THIAPOLYCYCLIC POLYAHL AND POLYURETHANES, POLYAMIDES AND POLYUREAS BASED THEREON

[75] Inventor: David W. Hughes, Midland, Mich.

[73] Assignee: The Dow Chemical Company, Midland, Mich.

[21] Appl. No.: 605,006

[22] Filed: Apr. 27, 1984

Related U.S. Application Data

[63] Continuation-in-part of Ser. No. 454,134, Dec. 29, 1982, abandoned.

[51] Int. Cl.$^4$ .................. C08G 18/32; C08G 69/26; C08G 63/62
[52] U.S. Cl. ........................................ 528/62; 528/68; 528/73; 528/337; 528/341; 528/372; 528/380; 549/9; 549/23
[58] Field of Search .................. 528/62, 337, 68, 73, 528/341, 372, 380; 549/9, 23

[56] References Cited

U.S. PATENT DOCUMENTS 3,644,415  2/1972  Weil et al. ........................ 260/327

FOREIGN PATENT DOCUMENTS 1061472  3/1967  United Kingdom .
1061473  3/1967  United Kingdom .

OTHER PUBLICATIONS

Lautenschlaeger, Can. Jour. Chem. vol. 44, No. 23, (1966), pp. 2813–2817.
Vincent et al., Rec. des Trav. Chim. des Pays–Bas, vol. 95, No. 19 (1976), pp. 236–237.
Cope et al., Jour. Org. Chem. vol. 34, No. 7, (1969), pp. 2231–2234.
Weil et al., Jour. Org. Chem. vol. 31, No. 6 (1966), pp. 1669–1679.
Vincent et al., Tetrahedron Let. No. 24 (1975), pp. 1989–1992.
Corey et al., Jour. Org. Chem. vol. 31, No. 6 (1966), pp. 1663–1668.
Condensed Chemical Dictionary, 5th Ed., Reinhold, N.Y. (1956), pp. 881–882.

*Primary Examiner*—Herbert S. Cockeram

[57] ABSTRACT

Alkyl-substituted thiapolycyclic polyahls such as dimethyl-9-thiabicyclononane diamines form polymers that have improved physical properties.

19 Claims, No Drawings

ALKYL-SUBSTITUTED THIAPOLYCYCLIC POLYAHL AND POLYURETHANES, POLYAMIDES AND POLYUREAS BASED THEREON

CROSS-REFERENCE TO RELATED APPLICATION

This application is a continuation-in-part to parent application Ser. No. 454,134 (incorporated herein by reference), filed Dec. 29, 1982, and now abandoned.

BACKGROUND OF THE INVENTION

This invention relates to alkyl-substituted thiapolycyclic polyahls which have utility as monomers in making polyamides and other polymers.

A polymer is a large molecule built up by the repetition of small, simpler chemical units called monomers. The character of the monomer unit has a strong effect on the physical and chemical properties of the polymer. For example, it is common to incorporate a para-phenylene group into a monomer to add rigidity to the polymer chain. This can engender desirable properties in the polymer such as: raising the melting point, increasing the stress-strain property ratios and improving the heat distortion performance.

The incorporation of aromatic nuclei in polymer chains, however, has its drawbacks. Polymers containing aromatic nuclei are susceptible to deterioration. They may stiffen and become brittle, change color, or yellow and weaken. Opaque fillers and light stabilizers and antioxidants are added to alleviate these problems. Aliphatic monomers yield polymers which are less susceptible to degradation but do not impart the same rigidity.

In view of the aforementioned deficiencies of both aliphatic and aromatic polymers, it would be highly desirable to provide a monomer which can form a polymer having ridigity, strength and thermal properties characteristic of aromatic polymers and resistance to degradation by light that is characteristic of aliphatic polymers.

SUMMARY OF THE INVENTION

In one aspect, the present invention is an alkyl-substituted thiapolycyclic polyahl having at least one thiapolycyclic moiety including the oxide or dioxide forms thereof which moiety bears at least one alkyl substituent and at least one active hydrogen substituent.

In another aspect this invention is a polymer of the aforementioned polyahl or an isomeric mixture thereof such as a polyamide, a polyurea, polyether, polyester or polyurethane. Surprisingly, such polymers having the aforementioned monomer or an isomeric mixture of such monomers having thiabicyclic moieties as the only monomeric components or as a part of a monomeric mixture with monomers which do not contain a thiabicyclic moiety exhibit an increase in rigidity and thermal properties comparable to that resulting from the introduction of an aromatic monomer.

In a third aspect, this invention is a method for polymerizing the diamine of this invention which method comprises contacting the diamine with a polyfunctional organic compound under conditions sufficient to cause the amine moieties of the diamine to react with the functional moieties of the polyfunctional organic compound.

DETAILED DESCRIPTION OF ILLUSTRATIVE EMBODIMENTS

The polyalkyl thiapolycyclic polyahl of this invention is an aliphatic compound having (1) a bridge system of at least two rings, (2) a sulfur-containing bridging group, (3) at least two active hydrogen (ahl) substituents and (4) at least one alkyl substituent, all of said substituents being bonded to carbons other than bridgehead carbons. The active hydrogen moiety suitable for this purpose is a moiety containing a hydrogen atom which, because of its position in the molecule, displays significant activity according to the Zerewitnoff test described by Woller in the *Journal of American Chemical Society*, Vol. 49, page 3181 (1927). Illustrative of such active hydrogen moieties are —COOH, —OH, —NH$_2$, —NH—, —CONH$_2$, —SH and —CONH—. Advantageously, the active hydrogen moieties are bonded to the same or different non-sulfur bridging groups. In addition, at least one and preferably two of the non-sulfur bridging groups bear a pendant lower alkyl moiety such as methyl, ethyl or propyl, preferably methyl. Representative preferred thiapolycyclic polyahls include those having the formula:

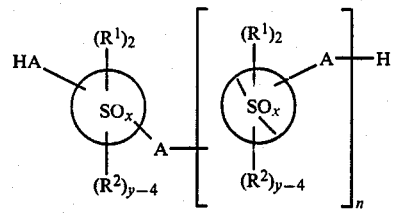

wherein A is a residue of an active hydrogen moiety such as —O—, —S—, —NR$^3$—,

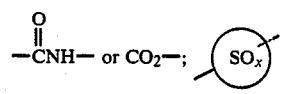

is a thiapolycyclic moiety having at least 6 carbons and a sulfur-containing bridging group and x is 0, 1 or 2; each R$^1$ is independently an alkyl group containing 1 to 3 carbon atoms; each R$^2$ is independently hydrogen or methyl provided that a least two R$^2$ are hydrogen; y is a number corresponding to available valences for the polycyclic ring; each R$^3$ is independently hydrogen, an aliphatic alkyl containing 1 to 20 carbon atoms or an inertly-substituted aliphatic alkyl containing 1 to 20 carbon atoms, with hydrogen being preferred; and n is 0, 1, 2 or 3. By "inert", it is meant that the substituent group will not react with the amine group or the thiabicyclic moiety, e.g., alkyl or alkoxy are such inert groups.

Preferably, in the aforementioned formula, AH is an amino moiety represented by —NR$^3$H. Most preferred are the diamines represented by the formula:

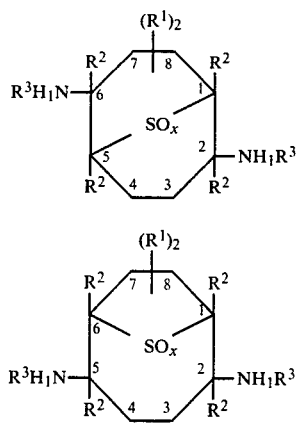

wherein each $R^1$ which may be the same or different, is an alkyl group containing 1 to 3 carbon atoms; each $R^2$, which may be the same or different is hydrogen or methyl, at least two $R^2$ are hydrogen; each $R^3$ which may be the same or different is hydrogen, an aliphatic alkyl group containing 1 to 20 carbon atoms or an inertly-substituted aliphatic alkyl group containing 1 to 20 carbon atoms; and x is 0, 1 or 2.

Examples of such preferred thiabicyclic diamines are dialkyl-9-thiabicyclononane diamine isomers and N-alkyl diamine derivatives thereof such as 2-endo-6-endo-2,6-diamino-4-endo-8-exo-4,8-dimethyl-9-thiabicyclo[3.3.1]nonane; 2-endo-6-endo-2,6-diamino-4-exo-8-exo-4,8-dimethyl-9-thiabicyclo[3.3.1]nonane; 2-endo-6-endo-2,6-diamino-4-endo-8-endo-4,8-dimethyl-9-thiabicyclo[3.3.1]nonane; 2-endo-6-endo-2,6-diamino-3-endo-7-endo-3,7-dimethyl-9-thiabicyclo[3.3.1]nonane; 2-endo-6-endo-2,6-diamino-3-exo-7-exo-3,7-dimethyl-thiabicyclo[3.3.1]nonane; 2-endo-6-endo-2,6-diamino-3-endo-7-exo-3,7-dimethyl-9-thiabicyclo[3.3.1]nonane; 2-endo-6-endo-2,6-diamino-3-exo-4-exo-3,4-dimethyl-9-thiabicyclo[3.3.1]nonane; 2-endo-6-endo-2,6-diamino-3-endo-4-exo-3,4-dimethyl-9-thiabicyclo[3.3.1]nonane; 2-endo-6-endo-2,6-diamino-3-exo-4-endo-3,4-dimethyl-9-thiabicyclo[3.3.1]nonane; 2-endo-6-endo-2,6-diamino-3-endo-4-endo-3,4-dimethyl-9-thiabicyclo[3.3.1]nonane; 2-endo-5-endo-2,5-diamino-7-endo-8-endo-7,8-dimethyl-9-thiabicyclo[4.2.1]nonane; 2-endo-6-endo-2,6-diamino-7-exo-1,7-dimethyl-9-thiabicyclo[3.3.1]nonane; 2-endo-6-endo-2,6-diamino-7-endo-1,7-dimethyl-9-thiabicyclo[3.3.1]nonane; 2-endo-6-endo-2,6-diamino-4-exo-1,4-dimethyl-9-thiabicyclo[3.3.1]nonane; 2-endo-6-endo-2,6-diamino-4-endo-1,4-dimethyl-9-thiabicyclo[3.3.1]nonane; 2-endo-5-endo-2,5-diamino-7-endo-1,7-dimethyl-9-thiabicyclo[3.3.1]nonane; and the N-alkyl derivatives of such diamines where the N-alkyl can be methyl, ethyl, isopropyl and the like, with the normally liquid mixtures of two or more such isomers being especially preferred.

Other isomers which are desirable include 2-endo-5-endo-2,5-diamino-7-exo-8-exo-7,8-dimethyl-9-thiabicyclo[4.2.1]nonane; 2-endo-5-endo-2,5-diamino-7-endo-8-exo-7,8-dimethyl-9-thiabicyclo[4.2.1]nonane; 2-endo-5-endo-2,5-diamino-3-exo-4-exo-3,4-dimethyl-9-thiabicyclo[4.2.1]nonane; 2-endo-5-endo-2,5-diamino-3-endo-4-endo-3,4-dimethyl-9-thibicyclo[4.2.1]nonane; 2-endo-5-endo-2,5-diamino-3-endo-4-exo-3,4-dimethyl-9-thiabicyclo[4.2.1]nonane; 2-endo-5-endo-2,5-diamino-3-endo-7-exo-3,7-dimethyl-9-thiabicyclo[4.2.1]nonane; 2-endo-5-endo-2,5-diamino-3-endo-7-endo-3,7-dimeth-yl-9-thiabicyclo[4.2.1]nonane; 2-endo-5-endo-2,5-diamino-3-endo-7-exo-3,7-dimethyl-9-thiabicyclo[4.2.1-]nonane; 2-endo-5-endo-2,5-diamino-3-exo-7-endo-3,7-dimethyl-9-thiabicyclo[4.2.1]nonane; 2-endo-6-endo-2,6-diamino-2-exo-7-exo-2,7-dimethyl-9-thiabicyclo[3.3.1]nonane; 2-endo-6-endo-2,6-diamino-2-exo-7-endo-2,7-dimethyl-9-thiabicyclo[3.3.1]nonane; 2-endo-6-endo-2,6-dimethyl-2-exo-4-exo-2,4-dimethyl-9-thiabicyclo[3.3.1]nonane; 2-endo-6-endo-2,6-diamino-2-exo-4-endo-2,4-dimethyl-9-thiabicyclo[3.3.1]nonane; 2-endo-5-endo-2,5-diamino-2-exo-4-exo-2,4-dimethyl-9-thiabicyclo[4.2.1]nonane; 2-endo-5-endo-2,5-diamino-2-exo-4-endo-2,4-dimethyl-9-thiabicyclo[4.2.1]nonane; 2-endo-5-endo-2,5-diamino-2-exo-7-exo-2,7-dimethyl-9-thiabicyclo[4.2.1]nonane; 2-endo-5-endo-2,5-diamino-2-exo-7-endo-2,7-dimethyl-9-thiabicyclo[4.2.1]nonane; 2-endo-5-endo-2,5-diamino-4-exo-1,4-dimethyl-9-thiabicyclo[3.3.1]nonane; 2-endo-5-endo-2,5-diamino-4-endo-1,4-diemthyl-9-thiabicyclo[3.3.1]nonane; and 2-endo-5-endo-2,5-diamino-7-exo-1,7-dimethyl-9-thiabicyclo[3.3.1]nonane.

Preparation of the most preferred thiabicyclo nonane diamines begins by reacting $C_5-C_8$ di-unsaturated hydrocarbons such as piperylene or 1,3-pentadiene; 1,3-hexadiene; 1,3-heptadiene; 5-methyl-1,3-hexadiene or mixtures of two or more of such aliphatic dienes represented by the formula:

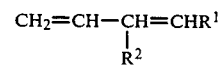

via cyclodimerization to form a 1,5-cyclooctadiene having the structure:

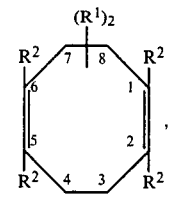

wherein $R^1$ and $R^2$ are as defined before. Alternatively, butadiene or isoprene can be cross-dimerized with piperylene or any of the other aforementioned dienes to produce the cyclic octadiene, or any two of said aforementioned dienes can be cross-dimerized to produce the desired cyclic octadiene.

Such cyclodimerization of a diene is known as taught by J. A. Berson et al., JACS, 98 (19), pp. 5937–68 (1976) (Chem. Abstr. 86:70,9559); and U. M. Dzhemilev et al., Neftekhimiya, 15 (6), pp. 819–24 (1975) (Chem. Abstr. 84:121,2456); all of which are incorporated herein by reference.

These processes yield a mixture of varying amounts of the following isomers:

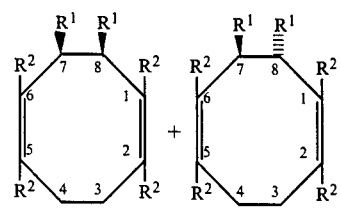

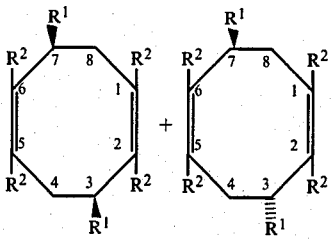

These isomers as well as isomers where one or two $R^2$ are $CH_3$ are collectively included as the aforementioned 1,5-cyclooctadiene used to prepare the most preferred thiabicyclononanes. Note that the $R^1$ groups are as defined above and are not attached to the carbons of the double bond. The double bonds are positioned between the 1 and 2 carbons and between the 5 and 6 carbons. The $R^1$ groups may be attached only to the 3, 4, 7 and 8 carbons. When $R^2$ is methyl, that group is attached to a carbon of the double bond. While the $R^2$ methyl groups may be attached to the carbons 1, 2, 5 or 6, only two of the $R^2$ groups can be methyl.

The cyclooctadienes may be converted to bicyclononanes (actually thiabicyclic dichlorides) by the reaction of the cyclooctadiene with sulfur dichloride or other sulfur chloride as disclosed in Weil et al. in *J. Org. Chem.*, 31 (6), pp 1669–1679 (1966); or Corey et al. in *J. Org. Chem.*, 31 (6), pp. 1663–1668 (1966); or Tolstikov et al. in *Zh. Org. Khim.*, 16 (7), pp. 1408–1418 (1980); or British Pat. Nos. 1,061,472 and 1,061,473; all of which are incorporated herein by reference.

This reaction is most conveniently practiced in the liquid phase, although it can also be accomplished in the vapor phase. The reaction is exothermic and, therefore, the reactants should be admixed by slow addition of one to the other, or, preferably, of both to a mutual solvent. Suitable solvents are any that are substantially inert to sulfur dichloride or other sulfur chloride and cyclooctadiene. Illustrative examples of suitable solvents include hydrocarbons such as toluene, benzene, hexane, cyclohexane, mineral spirits, chlorocarbons such as methylene chloride, carbon tetrachloride, ethylene dichloride, trichloroethylene, perchloroethylene, chlorobenzene, ethers such as diethyl ether, or miscellaneous solvents such as carbon disulfide, acetonitrile, thionyl chloride, acetic anhydride, acetyl chloride, nitromethane, nitrobenzene, and dimethyl formamide.

The reaction temperature is from $-40°$ C. to $150°$ C., however, the preferred range is between $-20°$ C. and $100°$ C. It is particularly convenient to employ reaction temperatures near ambient temperature, and to cool the reaction by water-jacketing the reactor using water, also at ambient temperature.

The reaction is very rapid and generally is complete within a few seconds to a few hours after the reactants are admixed, depending on temperature. Therefore, a catalyst is not necessary. Nonetheless, if desired, the reaction may be catalyzed by addition of Lewis acids (e.g., $FeCl_3$), iodine, light or peroxides.

While sulfur dichloride is the preferred reactant, sulfur monochloride may be employed to obtain the dichlorides, however, the use of sulfur monochloride results in a more complex reaction mixture which entails troublesome purification steps. Sulfur tetrachloride may also be used, with resultant formation of some thiabicyclononane having more than two chlorine atoms per mole.

A preferred method of making the dichloride is by admitting separate streams of the corresponding cyclooctadiene and sulfur dichloride, each dissolved in an appropriate solvent into a line containing a static mixer. The concentrations of the feed solutions and the ratio in which they are added into the reactor are controlled to ensure a slight molar excess of cyclooctadienes. The line is cooled to ensure a maximum reactor temperature of $-5°$ C. Preferably the sulfur dichloride is stabilized according to the method described in U.S. Pat. No. 3,071,441 which is incorporated herein by reference.

Such dichlorides are represented by the formulae:

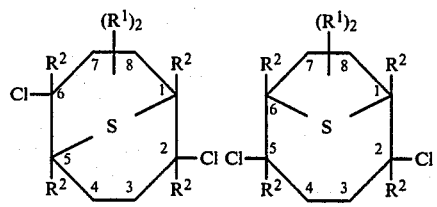

[3.3.1]   [2.4.1]

wherein the $R^1$ and $R^2$ groups are as defined before and the $R^1$ groups are connected to the 3, 4, 7 or 8 ring carbons, but not the carbons directly attached to either the sulfur or chlorine atoms (1, 2, 5, 6). Either or both of the [3.3.1] and [4.2.1] structures are found in the product as it has been found that the two structures are interconvertible during any reaction, even by merely dissolving in an ionizing solvent.

The dichloride is converted to the diamine using conventional procedures by contacting the dichloride with ammonia or a primary amine $R^3NH_2$ wherein $R^3$ is an aliphatic alkyl group containing 1–20 carbon atoms or an inertly-substituted aliphatic alkyl group containing 1–20 carbon atoms as $R^3$ is defined hereinbefore.

Examples of aliphatic alkyl groups are methyl, ethyl, n-propyl, isopropyl, dodecyl, etc. Examples of inert substituents are alkyl groups, cycloaliphatic groups, aromatic groups, alkyloxy groups, hydroxy and alkylhydroxy groups.

Preferably an excess of $NH_3$ to chloride is used. Most preferably the excess is at least about 17 equivalents of $NH_3$ per equivalent of chloro groups. Preferably the temperature of the ammonolysis is kept low to prevent formation of secondary amines. The temperature may be held at about $30°$ C. or less and preferably at about $20°$ C. or less.

The 9-oxides or 9,9-dioxides are the most preferred thiabicyclononanes, more generally called sulfoxides, or sulfones, respectively, and are prepared by the oxidation of the diamine using oxidizing agents. Illustrative oxidizing agents include hydrogen peroxide, peracetic acid, perbenzoic acid, perphthalic acid or other peroxy organic acids; nitric acid; nitrogen dioxide or tetraoxide; permanganates; chromic acid or dichromates; bromic acid or bromates; hypochlorous acid or hypochlorites; and ozone or molecular oxygen (preferably using a catalyst such as vanadium oxide or nitrogen dioxide).

The dimethyl thiabicyclononane diamines (DMTBCN) are generally obtained as isomeric mixtures and are therefore liquid at room temperature (normally liquid).

This improves the processability of the DMTBCN over the unsubstituted thiabicyclononane diamine which melts at about 70°–71° C. This DMTBCN diamine may be pumped in a liquid system at normal room temperature, whereas the unsubstituted diamine must be melted or dissolved to be pumped. This is a desirable characteristic for many polymerization systems which operate with liquid reactants.

Thiapolycyclic polyahls other than polyamines are prepared by similar techniques using the dichloride except that other reactants are substituted for the ammonia or amine. For example, in the preparation of the corresponding diol, the aforementioned dichloride is first reacted with potassium acetate and glacial acetic acid to form the corresponding bisacetate which is reacted with sodium methoxide in methanol to form the diol using conventional procedures for converting dichlorides to diols. In the preparation of the corresponding dithiol, the aforementioned dichloride is first reacted with thiourea in ethanol and water using conventional procedures. To this reaction mixture is added an aqueous solution of sodium hydroxide. The reaction mixture is heated at reflux, cooled and treated with hydrochloric acid and chloroform. The organic phase containing the desired dithiol is separated from the aqueous phase and the dithiol is recovered.

The polyamines, more preferably diamines, of the invention may be used to form polyamides, polyureas, polyurethane ureas, and as cross-linkers for epoxy polymers. In the polymers of the invention derived from the preferred thiabicyclononane diamines, the polymer has repeating units having the formula:

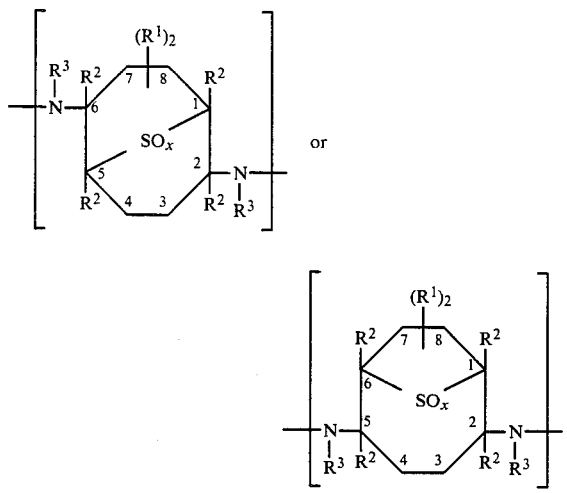

wherein $R^1$, $R^2$, $R^3$ and x are as defined hereinbefore.

Polymers and copolymers which are readily made from the aforementioned diamines include polyamide structures which contain monomer units such as:

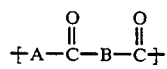

wherein A is the repeating unit, and B is a divalent hydrocarbon radical. Preferably B is an aliphatic chain such as $C_4H_8$ or $C_8H_{16}$, n-butyl, n-octyl. This polyamide is readily formed by contacting a DMTBCN diamine with a polyacid chloride of a polybasic acid such as adipoyl chloride, terephthaloyl chloride and isophthaloyl chloride using conventional procedures. Because the DMTBCN diamine is a liquid at room temperature, it is particularly useful in applications where liquid monomers are normally used.

Other polymers which may include the aforementioned repeating units also include the polyureas such as:

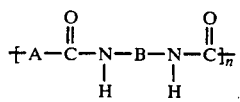

wherein A, B and n are as defined before. Preferably B is $C_6H_{12}$.

The polyurea is readily formed by contacting the alkyl-substituted thiapolycyclic diamine with an organic polyisocyanate such as aromatic, aliphatic and cycloaliphatic polyisocyanates and combinations thereof. Representative of these types are the diisocyanates such as m-phenylene diisocyanate, tolylene-2,4-diisocyanate, tolylene-2,6-diisocyanate, hexamethylene-1,6-diisocyanate, tetramethylene-1,4-diisocyanate, cyclohexane-1,4-diisocyanate, hexahydrotolylene diisocyanate (and isomers), naphthylene-1,5-diisocyanate, 1-methoxyphenyl-2,4-diisocyanate, diphenylmethane-4,4-diisocyanate, 4,4'-biphenylene diisocyanate, 3,3'-dimethoxy-4,4'-biphenyl diisocyanate, 3,3'-dimethyl-4,4'-biphenyl diisocyanate, and 3,3'-dimethyldiphenylmethane-4,4'-diisocyanate; the triisocyanates such as 4,4',4''-triphenylmethane triisocyanate, polymethylene polyphenylisocyanate and tolylene-2,4,6-triisocyanate; and the tetraisocyanates such as 4,4'-dimethyldiphenylmethane-2,2',5,5'-tetraisocyanate. Also suitable are diisocyanates of thiabicyclononanes. Especially useful due to their availability and properties are tolylene diisocyanate, diphenylmethane-4,4'-diisocyanate and polymethylene polyphenylisocyanate.

Crude polyisocyanates may also be used in the practice of the present invention, such as crude toluene diisocyanate obtained by the phosgenation of a mixture of toluenediamines or crude diphenylmethylene diisocyanate obtained by the phosgenation of crude diphenylmethylenediamine. The preferred undistilled or crude isocyanates are disclosed in U.S. Pat. No. 3,215,652.

Polyurethanes are readily formed by reacting the aforementioned polyisocyanates with alkyl-substituted thiapolycyclic polyols described hereinbefore. Usually such urethane reactions are carried by conventional procedures in the presence of known urethane catalysts such as tertiary amines, e.g., triethylenediamine. Known techniques may be used. Because the diamines are liquid at room temperature and because the molecule is sterically hindered, reaction with polyisocyanates is sufficiently slowed to allow preparation of such polymers. In particular, it is notable that when $R^3$ is not hydrogen, this reaction proceeds at a desirable rate.

Accordingly, other aspects of this invention are such polymers wherein a characterizing amount of repeating units of the above formulae are incorporated and a method for making them. By a characterizing amount, it is meant an amount of the aforementioned repeating units are present in the polymer so that the polymer exhibits properties such as rigidity and thermal resistance resulting from the presence of the monomer. Preferably, the polymer has at least 0.5 mole percent of the aforementioned repeating units, more preferably at least 10 mole percent, most preferably at least about 40 mole percent up to about 100 mole percent.

The polymers formed with the above-described monomers units have utility as coatings, films and castings. Surprisingly, such polymers may exhibit mechanical properties superior to those in which aromatic groups have been incorporated into the polymer backbone.

The following examples are given to illustrate the invention and should not be construed as limiting its scope. Unless otherwise indicated all parts and percentages set forth in this application are by weight.

EXAMPLE 1

A. Preparation of Dimethyl-1,5-cyclooctadiene

Nickel (II) acetonylacetonate dihydrate is dispersed in toluene and dried by azeotropic removal of the water (which is captured in a Dean-Stark trap). When no further water can be recovered, the dark green toluene solution of nickel (II) acetonylacetonate (Ni (II) acac) is evaporated to dryness, giving anhydrous Ni (II) acac. A 1000-ml three-necked round-bottom flask is equipped with a heating mantle, a magnetic stirbar and stirrer, a thermometer adaptor and thermometer, a stopcock-protected rubber septum, and a distillation head which was connected to give a nitrogen blanket on the system. The flask is then charged with 120 ml of toluene, 4.35 g (0.017 mole) of anhydrous Ni (II) acac, and 9.36 g (0.0173 mole) of tris(orthophenylphenyl)phosphite, and about 40 ml of toluene are removed by distillation to dry the system. The apparatus is allowed to cool, the distillation head replaced with a reflux condenser and nitrogen inlet/outlet (to maintain a nitrogen blanket), and 448.2 g of piperylene concentrate (containing 52 percent piperylene; 3.43 moles of piperylene), which had been distilled away from sodium metal, were added. The heating mantle is replaced with an ice bath, and the contents of the flask are cooled to below 10° C. At this point, 14.30 g of 25 percent w/v triisobutyl aluminum in toluene (0.0179 mole) is slowly added dropwise, causing the green solution to gradually turn yellowish brown. When addition is complete, the ice bath is replaced with a heating mantle and the reaction mixture is allowed to warm to room temperature. Heating is then begun to achieve reflux (color now bright red-orange) for about 60 hours. Gas chromatography of the reaction mixture shows that conversion is at least 70 percent. The apparatus is then fitted with a 100-cm Vigreux column and the reaction mixture fractionally distilled, the fraction distilling at about 75° C. at 60 Torr being collected as product. Yield is approximately 90 percent based on converted piperylene.

B. Preparation of Dimethyl Thiabicyclononane

The cyclooctadiene of Example 1 is used as the starting material. This example describes a continuous process set-up. The reactor used is a static in-line mixer which is jacketed. A 50:50 by volume mixture of ethylene glycol and water at −30° C. is circulated through the jacket. Separate inlets are provided ahead of the reaction zone for cyclooctadiene and sulfur dichloride reactant solutions. An outlet valve is provided after the reaction zone to remove products.

Dimethyl-1,5-cyclooctadiene (850 ml) (730 g, 5.36 moles DMCOD) containing about 12 percent other piperylene dimers is mixed with 175 ml of methylene chloride and connected to one inlet. Sulfur dichloride (355 ml) (575 g, 5.58 moles) dissolved in 3,600 ml of methylene chloride is attached to the second inlet.

Both reactants are fed to the reactor simultaneously. The DMCOD solution is fed at about 45 ml/min. The sulfur dichloride solution is fed at about 172 ml/min. The feeds are exhausted in about 23 minutes. During the reaction time, the temperature inside the reaction zone rises 11° C. Products are removed from the reaction zone at the same rate that they are added. When the feeds are exhausted the reaction zone is flushed with methylene chloride. The methylene chloride is evaporated from the product to give a black oil. Distillation of this oil at 85° C.-95° C. and 0.05-0.1 mm Hg gives about 1,100 g of a very light yellow oil. Infrared and nuclear magnetic resonance spectra are consistent with a mixture of dimethyl TBCN dichloride isomers.

C. Preparation of Dimethyl-Thiabicyclononane Diamines

A 2-liter, 316 stainless steel, stirred pressure vessel is well purged with dry nitrogen and charged with about 165 ml of dry heptane and 200 g (0.836 mole) of distilled dimethyl-dichloro-9-thiabicyclononanes. The vessel is then sealed and cooled to about −35° C. Gaseous ammonia is then introduced to the vessel and allowed to condense until at least 485 g (28.48 moles) have been collected. The vessel is then stirred and allowed to warm to about 25° C. After 2 hours at about 25° C., the vessel is vented to release unreacted ammonia. The dimethyl-thiabicyclononane diamine dihydrochlorides are obtained as a slurry in heptane; this slurry is transferred to a 5000-ml flask which is equipped with a mechanical stirring assembly, a Dean-Stark trap with condenser and nitrogen inlet/outlet (to provide a nitrogen blanket) and a pressure-compensating addition funnel. To the slurry is added 2 liters of fresh heptane and the mixture is heated to about 95° C. The addition funnel is charged with 1.75 liters of 1N aqueous sodium hydroxide; this is added to the stirred, hot mixture, resulting in the liberation of some $NH_3$. The flask is then reheated to achieve reflux, and water removed through the Dean-Stark trap as a result of the heptane-water azeotrope. When all the water has been removed, the mixture is filtered while hot and the filtrate evaporated to give dimethyl-thiabicyclononane diamines as a lightly-colored oil, in quantitative yield (based on the starting dimethyl-dichloro-9-thiabicyclononanes). This oil can be distilled in a Kugelrohr distillation apparatus at 90° C.-95° C. (air bath temperature) and 0.1-0.2 mm Hg, to give a nearly water-white liquid product. Infrared and nuclear magnetic resonance are consistent with a mixture of dimethyl-9-thiabicyclononane diamine isomers. A titration of this material in deionized water using 0.520N HCl gives an equivalent weight of about 99.8-100.4 (theory 100.2) g/equivalent.

When $R^3$ is not hydrogen, the amine may be substituted in the above reaction for the ammonia. The dimethyl thiabicyclononane dialkylamine will form in a similar manner. For example, a bis(isopropylamino)-dimethyl thiabicyclononane may be made.

EXAMPLE 2

Polyurethane Urea Made with Dimethyl-9-thiabicyclononane Diamines

A 207-g portion of dimethyl-9-thiabicyclononane diamines, 5910.2 g of a glycerine-initiated polyalkylene polyol made from propylene oxide with sufficient ethylene oxide terminal groups to yield 80 percent of primary hydroxyl based on the total number of hydroxyls and having a weight average molecular weight (Mw) of 4800–5000 (sold by The Dow Chemical Company under the tradename VORANOL® 4702) and 2370 g of ethylene glycol are weighed into the B-side storage tank of an Accuratio Co. VR-40® (trademark of Accuratio Co.) lab scale RIM (Reaction Injection Molding) machine; the A-side is charged with 12,402 g of ISONATE® 143L (trademark of the Upjohn Co., Inc.) (a liquid form of diphenylmethane diisocyanate). Both sides are stirred and recirculated at 37° C. to ensure thorough mixing, particularly of the B-side. The machine is calibrated to give an A/B weight ratio of between 1.44 and 1.47, resulting in an isocyanate/reactive hydrogen index of about 1.05. The RIM unit is then activated to fill a heated (80° C.) plaque mold, 10"×10"×⅛". The plaque is held in the heated mold for 1 minute, then post-cured at 150° C. for 1 hour. Such plaques are tough and flexible. Samples will test to give a tensile strength of about 4,000 psi, a tensile modulus of about 105,000 psi, a flexural strength of about 4,600 psi, and a flexural modulus of about 115,000 psi. Polyurethane ureas may similarly be made when $R^3$ is not hydrogen. For example, when $R^3$ is isopropyl. Such polymer may be relatively slow curing, permitting complete mixing prior to reaction and uniform properties in the polymer artifacts.

What is claimed is:

1. An alkyl-substituted thiabicyclic polyahl or mixture thereof which is represented by the structural formula:

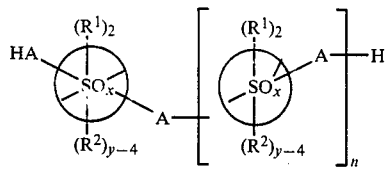

wherein A is a residue of an active hydrogen moiety

is a thiapolycyclic moiety having at least 6 carbons and a sulfur-containing bridging group and x is 0, 1 or 2; each $R^1$ is independently an alkyl group containing 1 to 3 carbon atoms, each $R^2$ is independently hydrogen or methyl provided that at least two $R^2$ are hydrogen; y is a number corresponding to available valences for the polycyclic ring; each $R^3$ is independently hydrogen, an aliphatic alkyl containing 1 to 20 carbon atoms or an inertly-substituted aliphatic alkyl containing 1 to 20 carbon atoms, with hydrogen being preferred; and n is 0, 1, 2 or 3.

2. The polyahl of claim 1 which is represented by one of the structural formulas:

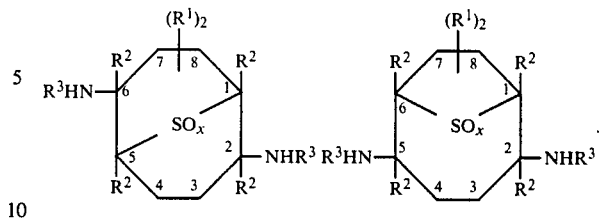

3. The polyahl of claim 1 which is a mixture of dialkyl-9-thiabicyclononane diamine isomers.

4. A thiabicyclononane diamine of the formula:

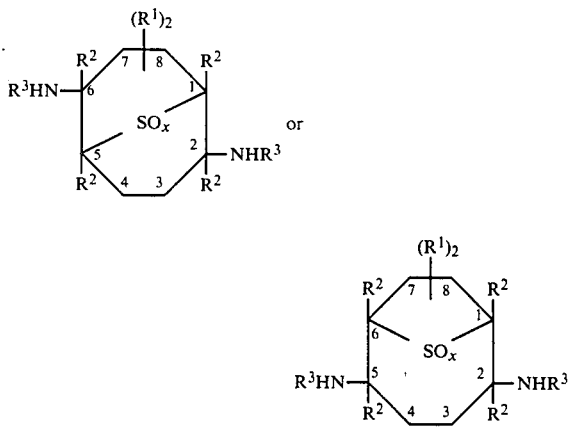

which is liquid at room temperature and wherein each $R^1$, which may be the same or different, is an alkyl group containing 1 to 3 carbon atoms; each $R^2$, which may be the same or different is hydrogen or methyl, provided that at least two $R^2$ are hydrogen; each $R^3$ which may be the same or different is hydrogen, an aliphatic alkyl group containing 1 to 20 carbon atoms or an inertly-substituted aliphatic alkyl radial group containing 1 to 20 carbon atoms; and x is 0, 1 or 2.

5. The diamine of claim 4 wherein all $R^2$ are hydrogen.

6. The diamine of claim 5 wherein x is zero.

7. The diamine of claim 6 wherein each $R^1$ is methyl.

8. The diamine of claim 6 wherein each $R^1$ is attached to the 3, 4, 7 or 8 carbon atoms.

9. The diamine of claim 8 wherein there is a mixture of isomers wherein $R^1$ groups are attached to different carbon atoms in different nonane rings.

10. A thiabicyclononane diahl of the formula

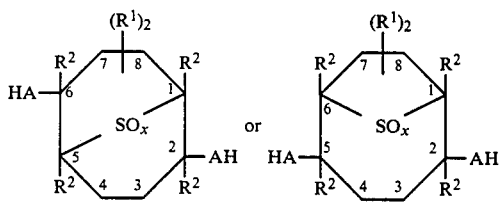

which is liquid at room temperature and wherein A is a residue of an active hydrogen moiety selected from the group consisting of —O—, —S—, —NR³—, $$-\overset{\overset{\displaystyle O}{\|}}{C}HN-$$

and —CO$_2$—, each R$^1$, which may be the same or different, is an alkyl group containing 1 to 3 carbon atoms; each R$^2$, which may be the same or different is hydrogen or methyl, provided that at least two R$^2$ are hydrogen; each R$^3$ which may be the same or different is hydrogen, an aliphatic alkyl group containing 1 to 20 carbon atoms or an inertly-substituted aliphatic alkyl radical group containing 1 to 20 carbon atoms; and x is 0, 1 or 2.

11. A polymer having repeating units of the formula:

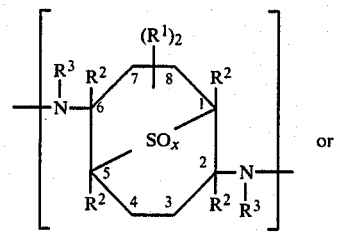

or

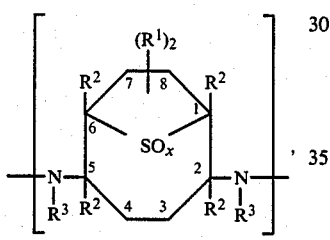

wherein each R$^1$, which may be the same or different, is an alkyl group containing 1 to 3 carbon atoms wherein each R$^1$ is attached to the 3, 4, 7 or 8 carbon atom and to different carbon atoms in different nonane rings; each R$^2$, which may be the same or different is hydrogen or methyl, at least two R$^2$ are hydrogen; each R$^3$ which may be the same or different is hydrogen, an aliphatic alkyl group containing 1 to 20 carbon atoms or an inertly-substituted aliphatic alkyl group containing 1 to 20 carbon atoms; and x is 0, 1 or 2.

12. The polymer of claim 11 wherein all R$^2$ are hydrogen.

13. The polymer of claim 12 wherein x is zero.

14. The polymer of claim 13 wherein each R$^1$ is methyl.

15. The polymer of claim 11 wherein at least about 0.5 mole percent of the monomer units is present.

16. The polymer of claim 15 wherein at least about 10 mole percent of the monomer units is present.

17. The polymer of claim 16 wherein at least about 40 mole percent of the monomer units is present.

18. The polymer of claim 15 wherein the polymer is a polyamide or a polyurea.

19. A method of forming a polymer comprising reacting a monomer, liquid at room temperature, of the formula:

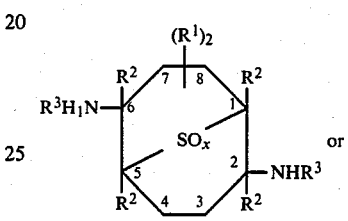

or

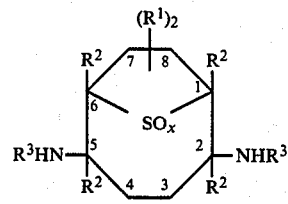

wherein each R$^1$, which may be the same or different, is an alkyl group containing 1 to 3 carbon atoms; each R$^2$ which may be the same or different is hydrogen or methyl, at least two R$^2$ are hydrogen; each R$^3$ which may be the same or different is hydrogen, an aliphatic alkyl group containing 1 to 20 carbon atoms or an inertly-substituted aliphatic alkyl group containing 1 to 20 carbon atoms; and x is 0, 1 or 2; with a polybasic acid, a polybasic acid ester, a polybasic acid chloride, or a polyisocyanate.

* * * * *